US009778175B2

(12) United States Patent
Chen et al.

(10) Patent No.: US 9,778,175 B2
(45) Date of Patent: Oct. 3, 2017

(54) HIGH-SENSITIVITY TERAHERTZ MICRO-FLUIDIC CHANNEL SENSOR AND PREPARATION METHOD THEREOF

(71) Applicant: Suzhou Institute of Nano-Tech and Nano-Bionics, Chinese Academy of Sciences, SIP Suzhou (CN)

(72) Inventors: Qin Chen, SIP Suzhou (CN); Fuhe Sun, SIP Suzhou (CN)

(73) Assignee: Suzhou Institute of Nano-Tech and Nano-Bionics, Chinese Academy of Sciences, Suzhou (CN)

( * ) Notice: Subject to any disclaimer, the term of this patent is extended or adjusted under 35 U.S.C. 154(b) by 0 days.

(21) Appl. No.: 14/896,192

(22) PCT Filed: Jul. 11, 2014

(86) PCT No.: PCT/CN2014/082018
§ 371 (c)(1),
(2) Date: Dec. 4, 2015

(87) PCT Pub. No.: WO2015/010545
PCT Pub. Date: Jan. 29, 2015

(65) Prior Publication Data
US 2016/0116402 A1    Apr. 28, 2016

(30) Foreign Application Priority Data

Jul. 25, 2013  (CN) .......................... 2013 1 0316628

(51) Int. Cl.
*G01N 21/03*    (2006.01)
*G01N 21/3581*    (2014.01)
(Continued)

(52) U.S. Cl.
CPC .... *G01N 21/3581* (2013.01); *B01L 3/502707* (2013.01); *B01L 3/502715* (2013.01);
(Continued)

(58) Field of Classification Search
CPC ... G01N 21/3581; G01N 21/3586; B01L 3/50
See application file for complete search history.

(56) References Cited

U.S. PATENT DOCUMENTS

| 6,167,910 B1 * | 1/2001 | Chow ................. B01J 19/0093 137/526 |
| 2006/0275185 A1 * | 12/2006 | Tonkovich ........... B01J 19/0093 422/130 |

(Continued)

FOREIGN PATENT DOCUMENTS

| CN | 101360986 A | 2/2009 |
| CN | 101978248 A | 2/2011 |
| CN | 103499534 A | 1/2014 |

OTHER PUBLICATIONS

Dong et al. "An Absorptive Filter Using Microfluidic Switchable Metamaterials". Solid-State Sensors, Actuators and Microsystems Conference (Transducers), 2011 16th International, published: Aug. 1, 2011.*

(Continued)

*Primary Examiner* — Casey Bryant
(74) *Attorney, Agent, or Firm* — Wang Law Firm, Inc.

(57) ABSTRACT

A high-sensitivity terahertz micro-fluidic channel sensor and a preparation method thereof. The sensor includes a substrate and a cover layer, respectively provided with a metal plane reflector and a metal microstructure layer; a micro-fluidic channel is formed between the metal plane reflector and the metal microstructure layer; and when the micro-fluidic channel tests liquid, a composite structure formed of the metal microstructure layer, the test liquid and the metal plane reflector shows good absorption properties. The method includes forming a metal plane reflector and a metal microstructure layer on a substrate and a cover layer, respectively; fixedly connecting the substrate to the cover layer, and forming a closed micro-fluidic channel between the (Continued)

substrate and the cover layer; and forming a through via, communicated to the micro-fluidic channel, on the substrate and/or the cover layer, to form a flow channel for transferring liquid to be tested to or from the sensor.

15 Claims, 21 Drawing Sheets

(51) Int. Cl.
      *B23K 31/02*     (2006.01)
      *C23C 14/35*     (2006.01)
      *G01N 21/3577*   (2014.01)
      *G01N 21/05*     (2006.01)
      *B01L 3/00*      (2006.01)

(52) U.S. Cl.
     CPC .............. *B23K 31/02* (2013.01); *C23C 14/35* (2013.01); *G01N 21/05* (2013.01); *G01N 21/3577* (2013.01); *B01L 2300/0663* (2013.01); *G01N 21/0303* (2013.01); *G01N 2021/0346* (2013.01)

(56) References Cited

U.S. PATENT DOCUMENTS

2010/0233825 A1*  9/2010  Yamada ................ G01N 21/554
                                                            436/525
2015/0198517 A1*  7/2015  Simpson ............ G01N 15/1459
                                                            209/552
2016/0231274 A1*  8/2016  Tirapu
                               Azpiroz ........... G01N 27/44791

OTHER PUBLICATIONS

Dong et al. "An Absorptive Filter Using Microfluidic Switchable Metamaterials," Solid-State Sensors, Actuators and Microsystems Conference (Transducers), 2011 16th International: accessed Mar. 15, 2017. <http://ieeexplore.ieee.org/document/5969421/#full-text-section>.*

International Search Report of international application PCT/CN2014/082018.

* cited by examiner

HIGH-SENSITIVITY TERAHERTZ MICRO-FLUIDIC CHANNEL SENSOR AND PREPARATION METHOD THEREOF

TECHNICAL FIELD OF THE INVENTION

The present invention relates to a sensor and a preparation method thereof, in particular to a sensor for improving the sensitivity of liquid sensing by combining the micro-fluidic technology and utilizing the resonance absorption properties of a microstructure to the terahertz, and a preparation method thereof, belonging to the technical field of sensors.

BACKGROUND OF THE INVENTION

At present, biomedicine, environmental monitoring, food safety, even national defense and other fields all require high-sensitivity sensors urgently. Optics-based sensors, due to their high sensitivity, wide application range, easy operation, and abundant function, have been developed greatly. Label-free optical detection technology, which is to sense by perceiving change in the refractive index of samples to be tested, without requiring any processing on the samples, so that the samples in a natural state may be detected in real time and quantitatively at low cost, has been widely used. Generally, such an optical label-free sensor runs in both the visible band and the near-infrared band. In recent years, terahertz band sensors have attracted people's attention. The terahertz frequency (0.1 THz to 10 THz) is between infrared and microwave, and many bio-macromolecules have a vibration frequency within the terahertz band and a characteristic absorption peak. Therefore, the terahertz sensing shows better identification capacity and higher sensitivity. Additionally, specifically the optical sensing of liquid samples, in order to realize sensing detection with fewer samples and to more effectively control reaction and separation between micro samples and the like, the micro-fluidic channel technology is developed rapidly. Currently, the combination of the micro-fluidic channel with the terahertz technology becomes one tendency of the optical label-free sensing technology.

A terahertz micro-fluidic biosensor based on micro-strip transmission lines was reported in the Applied Physics Letters, Vol. 93, P182904, 2008. This sensor realizes sensing, by detecting change in optical transmission properties resulted from the coupling between evanescent waves on the surface of the micro-strip lines and the liquid sample in the micro-fluidic channel. A terahertz micro-fluidic sensor based on planar waveguide resonators was reported in the Applied Physics Letters, Vol. 95, P171113, 2009. This sensor improves the sensitivity of detection by using the effect of resonators. Biosensing by a perfect absorber made of meta-material was reported in the Nano Letters, Vol. 10, P2342, 2010. Enhancement of sensitivity of a terahertz detector by the near-field localization properties of a metal micro-nano antenna structure was reported in the Optics Express, Vol. 20, P5052, 2012. A sensor based on metamaterial was proposed in the Applied Physics Letters, Vol. 100, P221101, 2012. The aforementioned technologies all realize sensing, based on superposition between samples to be tested and the near-field evanescent waves of a resonant structure, by measuring change in the evanescent waves along with change in the refractive index of the samples to be tested. Therefore, the sensing is limited to the degree of superposition between the evanescent waves and the liquid to be tested, and the improvement of sensitivity is limited.

SUMMARY OF THE INVENTION

In view of deficiencies in the prior art, an objective of the present invention is to provide a high-sensitivity terahertz micro-fluidic channel sensor and a preparation method thereof. This sensor realizes spatial superposition between electromagnetic-field localization and liquid to be tested in the micro-fluidic channel at a resonance frequency, by establishing a resonance absorber formed of a metal plane reflector, a micro-fluidic channel and a metal microstructure, thereby improving the sensitivity of detection of the sensor.

In order to achieve the objective, the present invention employs the following technical solutions:

A high-sensitivity terahertz micro-fluidic channel sensor is provided, including a substrate having a metal plane reflector thereon and at least one cover layer having a metal microstructure layer thereon; at least one micro-fluidic channel, for allowing liquid to be tested to flow through, is formed between the metal plane reflector and the metal microstructure layer; and when the micro-fluidic channel has the liquid to be tested therein, a composite structure mainly formed of the metal microstructure layer, the liquid to be tested and the metal plane reflector shows, in the terahertz band, good absorption properties due to resonance.

As one of preferred implementations, the sensor includes more than two cover layers successively distributed in a direction perpendicular to the plane direction of the micro-fluidic channel; and a metal microstructure layer is provided on a surface, facing the plane reflector, of any of the cover layers; a micro-fluidic channel is formed between the metal plane reflector and an adjacent metal microstructure layer and between adjacent cover layers, respectively, and those micro-fluidic channels are communicated to each other.

Further, those micro-fluidic channels are communicated to each other in a direction perpendicular to the plane direction of the micro-fluidic channels, successively.

Further, the metal microstructure layer includes more than one periodic structure unit adhered on the cover layer.

Further, the period of the periodic structure unit is preferably 10 µm to 500 µm, and the thickness thereof is preferably 0.01 µm to 0.5 µm.

Further, metal used for forming the metal microstructure layer is at least selected from any one of gold, silver, copper, aluminum, titanium, nickel and chromium or a combination of more than two thereof.

Further, the thickness of the metal plane reflector is greater than 50 nm.

Further, metal used for forming the metal plane reflector is at least selected from any one of gold, silver, copper, aluminum, titanium, nickel and chromium or a combination of more than two thereof.

Further, the height of the micro-fluidic channel is preferably 1 µm to 10 µm, and the width thereof is preferably 100 µm to 5000 µm; and two ends of the micro-fluidic channel are communicated to a liquid inlet and a liquid outlet of the sensor, respectively.

Further, material for the substrate is at least selected from any one of silicon, gallium arsenide, glass, polydimethylsiloxane, polypropylene, polyethylene, polytetrafluoroethylene, polymethylpentene and polyimide.

Further, material for the cover layer is at least selected from any one of silicon, gallium arsenide, glass, polydimethylsiloxane, polypropylene, polyethylene, polytetrafluoroethylene, polymethylpentene and polyimide.

Further, the substrate is connected to an adjacent cover layer by bonding, adjacent cover layers are connected to each other by bonding, and in this way, a closed micro-fluidic channel is formed between the substrate and an adjacent cover layer and between adjacent cover layers, respectively.

Further, the sensor further includes a medium protection layer formed on the metal plane reflector and/or the metal microstructure layer.

Further, the thickness of the medium protection layer is preferably 0 nm to 100 nm.

Further, material used for forming the medium protection layer is at least selected from any one of silicon dioxide, silicon nitride, aluminum oxide and SU-8 photoresist.

A preparation method of the high-sensitivity terahertz micro-fluidic channel sensor, including:

forming a metal plane reflector and a metal microstructure layer on a substrate and at least one cover layer, respectively;

fixedly connecting the substrate to the at least one cover layer, and forming at least one closed micro-fluidic channel between the substrate and the at least one cover layer; and forming a through via, communicated to the micro-fluidic channel, on the substrate and/or the cover layer, to form a flow channel for inputting or outputting liquid to be tested to or from the sensor.

As one of the preferred implementations, the preparation method may include:

(1) forming the metal plane reflector on the substrate by a metal film deposition process;

(2) forming the metal microstructure layer, or the metal microstructure layer and a sidewall of the micro-fluidic channel, on the at least one cover layer by a micro-nano machining process;

(3) connecting the substrate to the at least one cover layer by bonding, and forming at least one closed micro-fluidic channel between the substrate and the at least one cover layer; and (4) then, forming a through via, communicated to the micro-fluidic channel, on the substrate and/or cover layer, physically or chemically.

Compared with the prior art, the present invention at least has the following advantages: by integrating a micro-fluidic channel between the metal plane reflector and the metal microstructure layer to together form a composite structure having resonance absorption properties (absorbency at a resonance frequency may be over 95% and almost 100%), the electromagnetic field is spatially localized in the micro-fluidic channel, due to the resonance effect, to be completely overlapped with the liquid to be tested, and becomes very sensitive to the refractive index of liquid to be tested in the micro-fluidic channel; and the detection of refractive index of liquid to be tested is limited to 0.0014 RIU (calculated assuming that the spectral resolution of a terahertz spectrometer is 5 GHz). Therefore, high-sensitivity detection may be realized, by detecting shifting of the resonance absorption frequency and change in the resonance absorbency.

BRIEF DESCRIPTION OF THE DRAWINGS

In order to explain the content of the present invention better, embodiments will be simply explained with reference to the accompanying drawings. The drawings are schematic views of idealized embodiments of the present invention. In order to show clearly, the thickness of layers and regions is exaggerated. The drawings, as schematic views, should not be regarded as strictly reflecting the proportional relation of geometries. The embodiments of the present invention should not be regarded as being limited to specific shapes of the regions shown in the drawings. The expression in the drawings is exemplary, and should not be regarded as limiting the scope of the present invention. In the drawings.

DETAILED DESCRIPTION OF THE INVENTION

One aspect of the present invention is to provide a high-sensitivity terahertz micro-fluidic channel sensor, the structure of which is at least selected from a substrate, a metal plane reflector, a micro-fluidic channel, a metal microstructure and a cover layer.

As one of preferred implementation, the sensor may further include a plurality of different metal microstructures and micro-fluidic channels cascaded in a direction perpendicular to the plane direction of the micro-fluidic channel.

Figure 2:
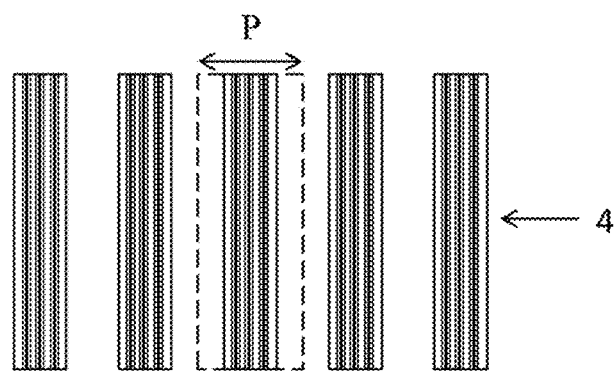
FIG. 2 is a schematic plan view of a one-dimensional periodic structure of a metal microstructure layer according to an optional implementation of the present invention.

The metal microstructure layer is in a periodic structure, the thickness of which is preferably 0.01 μm to 0.5 μm, and the period thereof is preferably 10 μm to 500 μm. The periodic structure may be an one-dimensional or two-dimensional plane periodic structure (referring to FIG. 2 to FIG. 3), including more than one periodic unit, the periodic unit being a simple unit or a combination of more than two simple units having the resonance absorption effect within different frequency ranges. Metal may be any one of gold, silver, copper, aluminum, titanium, nickel and chromium or a combination of several thereof.

The micro-fluidic channel, the height of which is preferably 1 μm to 10 μm and the width thereof is preferably 100 μm to 5000 μm, is formed by bonding from the cover layer containing the metal microstructure layer and the substrate containing a metal plane reflector. Two ends of the micro-fluidic channel are connected to an inlet and an outlet of the entire sensor by small holes passing through the cover layer or the substrate, respectively.

The thickness of the metal plane reflector is greater than 50 nm, and metal may be any one of gold, silver, copper, aluminum, titanium, nickel and chromium or a combination of several thereof.

Material for the substrate may be silicon, gallium arsenide, glass, polydimethylsiloxane, polypropylene, polyethylene, polytetrafluoroethylene, polymethylpentene and polyimide and the like.

Material for the substrate may be silicon, gallium arsenide, glass, polydimethylsiloxane, polypropylene, polyethylene, polytetrafluoroethylene, polymethylpentene and polyimide and the like.

The metal microstructure layer, the liquid to be tested in the micro-fluidic channel and the metal plane reflector form a composite structure which shows, in a narrowband of the terahertz band, good absorption properties due to resonance.

Another aspect of the present invention is to provide a preparation method of the high-sensitivity terahertz micro-fluidic channel sensor, including the following steps of:

(1) forming the metal plane reflector on the substrate by a metal film deposition process;

(2) forming a metal microstructure layer on the cover layer by a micro-nano machining process;

(3) connecting the substrate in (1) and (2) to the cover layer by bonding, and forming a closed micro-fluidic channel between the substrate and the cover layer; and (4) forming holes the substrate and/or the cover layer by chemical etching or mechanical drilling, and communicating the holes to the micro-fluidic channel.

Further, the metal film deposition process in (1) is a physical deposition process, for example, thermal evaporation, magnetron sputtering or electron beam evaporation.

Further, the micro-nano machining process in (2) includes photolithography/stripping, photolithography/etching or nanoimprint, or other processes.

Further, in the step (2), a sidewall of the micro-fluidic channel may be formed by machining on a thick cover layer.

Further, the bonding in the step (3) is intermediate layer bonding, wafer direct bonding and the like (Proceedings of The IEEE, Vol. 86, P1575, 1998).

Technical solutions of the present invention will be explained below in detail with reference to the related accompany drawings by some preferred embodiments.

Embodiment 1

Figure 1:
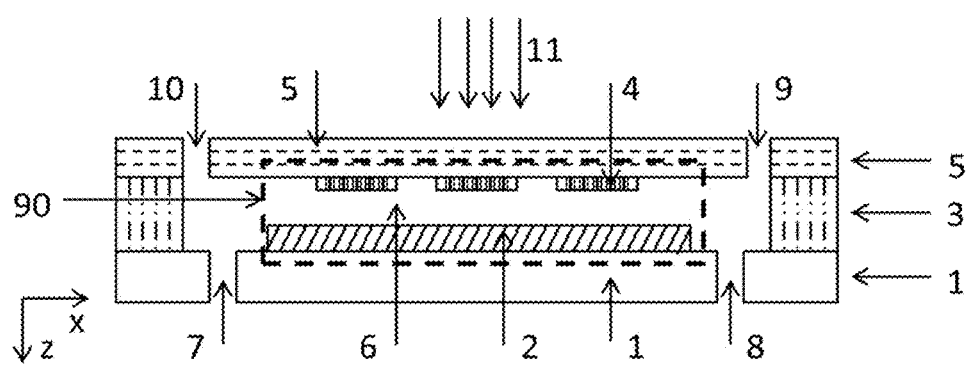
FIG. 1 is a schematic longitudinal cross-section view of a high-sensitivity terahertz micro-fluidic channel sensor according to an optional implementation of the present invention.
Figure 3:
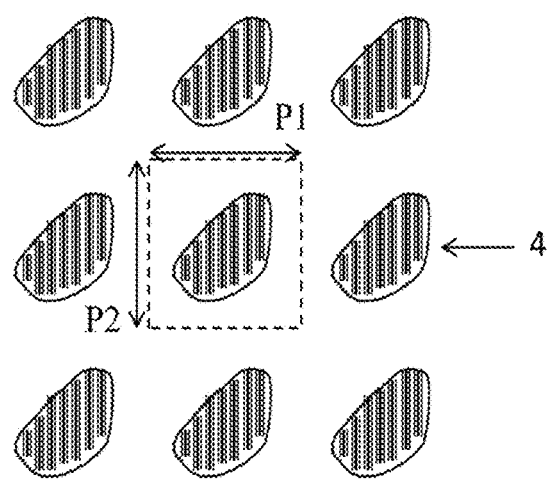
FIG. 3 is a schematic plan view of a two-dimensional periodic structure of the metal microstructure layer according to an optional implementation of the present invention.
Figure 5:
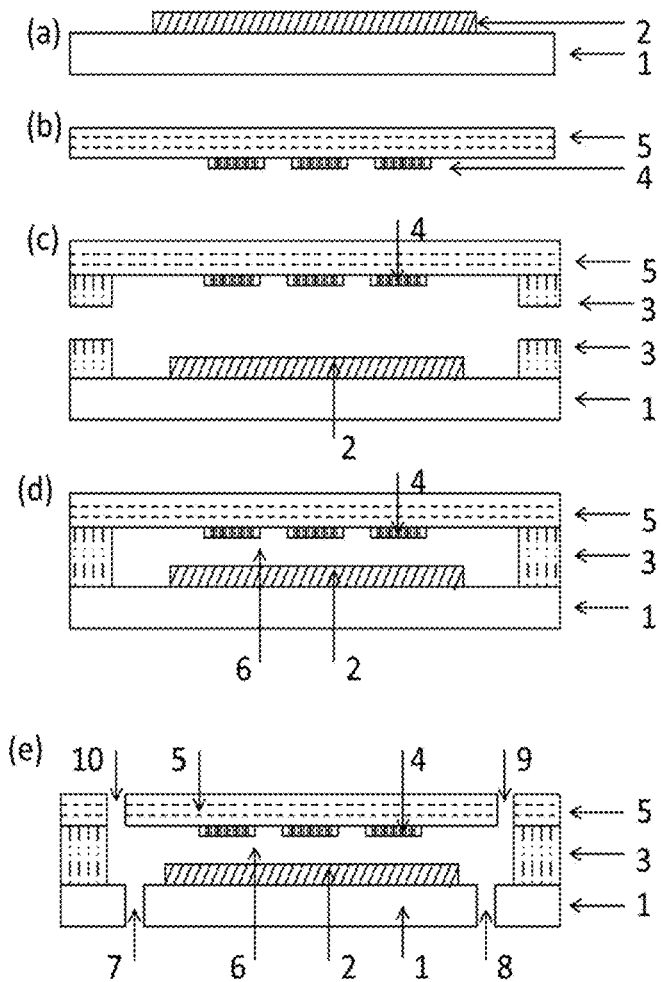
FIG. 5 is a process flowchart of a high-sensitivity terahertz micro-fluidic channel sensor according to an optional implementation of the present invention.

In this embodiment, description will given by taking the structural views shown in FIG. 1 and FIG. 3 and the process flowchart shown in FIG. 5 as an example. A preparation process of the high-sensitivity terahertz micro-fluidic channel sensor includes:

first, a metal plane reflector 2 is prepared on a substrate 1 by a metal film deposition process (FIG. 5(a));

next, a metal microstructure layer 4 is prepared on a cover layer 5 by micro-nano machining process, for example, photolithography, film deposition and stripping process (FIG. 5(b)), and then a bonding material layer 3 is prepared on the substrate 1 and the cover layer 5 by the micro-nano machining process (FIG. 5(c));

the substrate 1 is connected to the cover layer 5 by intermediate layer bonding, and a closed micro-fluidic channel 6 is formed between the substrate 1 and the cover layer 5 (FIG. 5(d)); and finally, inlets and outlets 7, 8, 9 and 10, communicated to the micro-fluidic channel, are formed on the substrate 1 or the cover layer 5 by etching or drilling (FIG. 5(e)).

Figure 10:
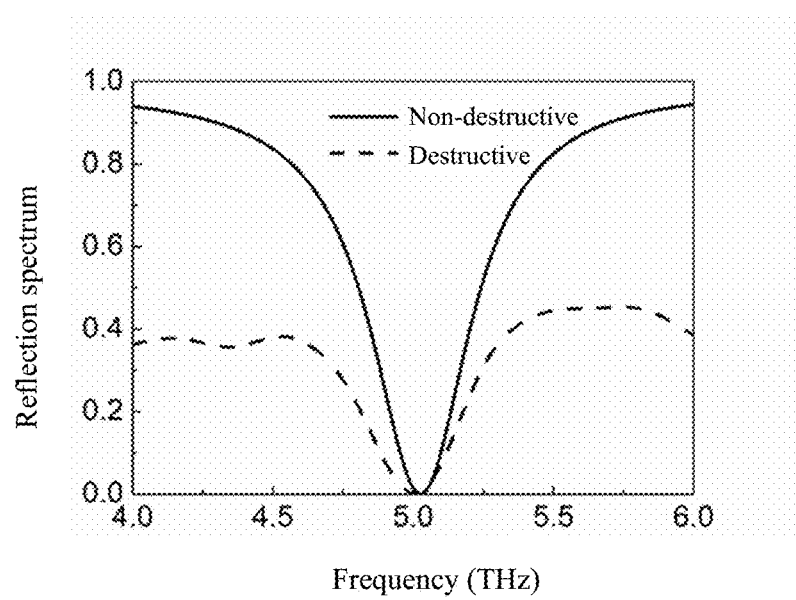
FIG. 10 is a reflection spectrum of terahertz sensors, when a cover layer is a non-destructive medium or a destructive medium, according to an optional implementation.

Preferably, in this embodiment, material for both the metal plane reflector 2 and the metal microstructure layer 4 may be Au, the refractive index is calculated by a Drude model, and the thickness of both the metal plane reflector 2 and the metal microstructure layer 4 is 0.2 μm. The metal microstructure layer 4, which is of a crisscross structure, has a period of 22 μm, an arm length of 15 μm, and an arm width of 6 μm. The height of a fluid channel 6 is 1 μm. Material for the cover layer 5 is PDMS. FIG. 10 shows a reflection spectrum of the terahertz sensor in a case where the PDMS is regarded as a non-destructive medium (with a refractive index of 1.45) and a destructive medium (referring to the Physical Review E, Vol. 75, P036614, 2007, for optical parameters). It can be seen that, the reflection spectra corresponding to the optical parameters of the two materials show the consistent resonance frequency, and the only difference is that the background reflectivity calculated based on the destructive medium parameter is low. Therefore, the evaluation on the sensitivity of sensors will not be influenced. Hence, a non-destructive model will be applied to the design of the embodiments hereinafter.

Figure 9:
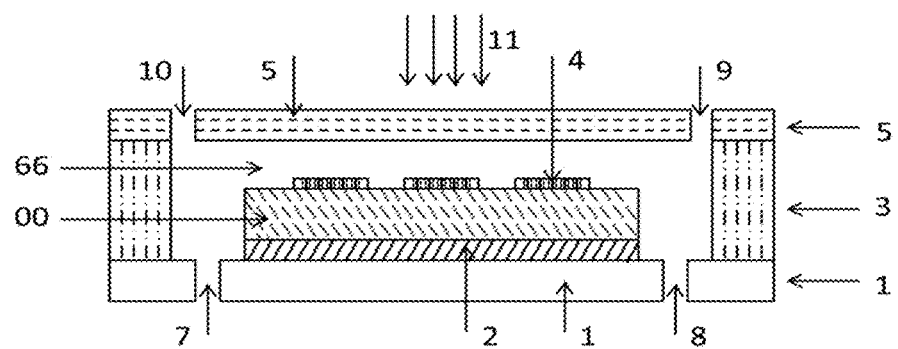
FIG. 9 is a schematic longitudinal cross-section view of a sensor (with the micro-fluidic channel integrated on a surface of the metal microstructure) used for comparing with the sensor of the embodiments of the present invention.
Figure 11A:
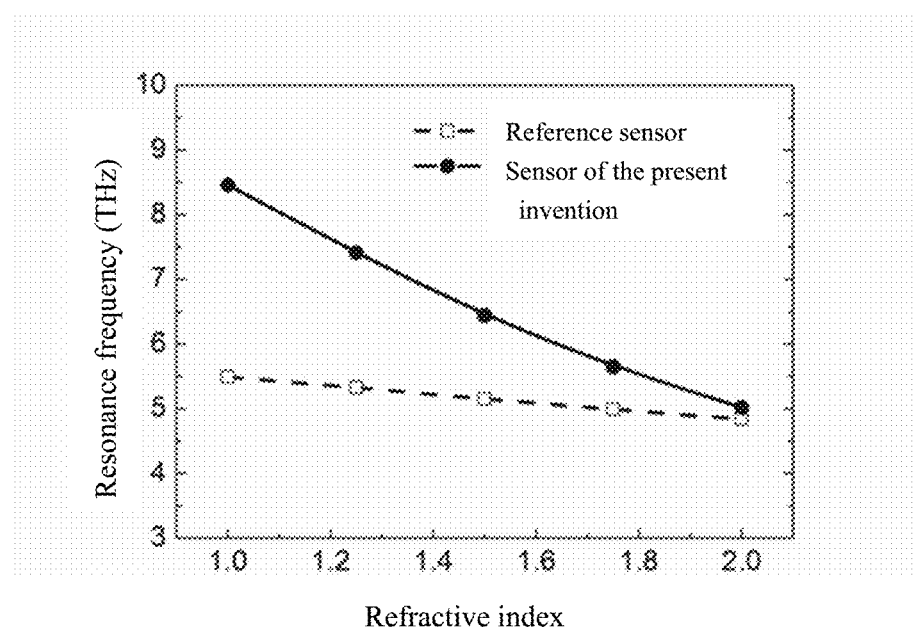
FIG. 11a to FIG. 11b are views showing the relation between the resonance frequency of the terahertz sensor and the refractive index of liquid, in a case where the cover layer is a non-destructive medium (a) and a case where the cover layer is a destructive medium (b), according to an optional implementation.
Figure 11B:
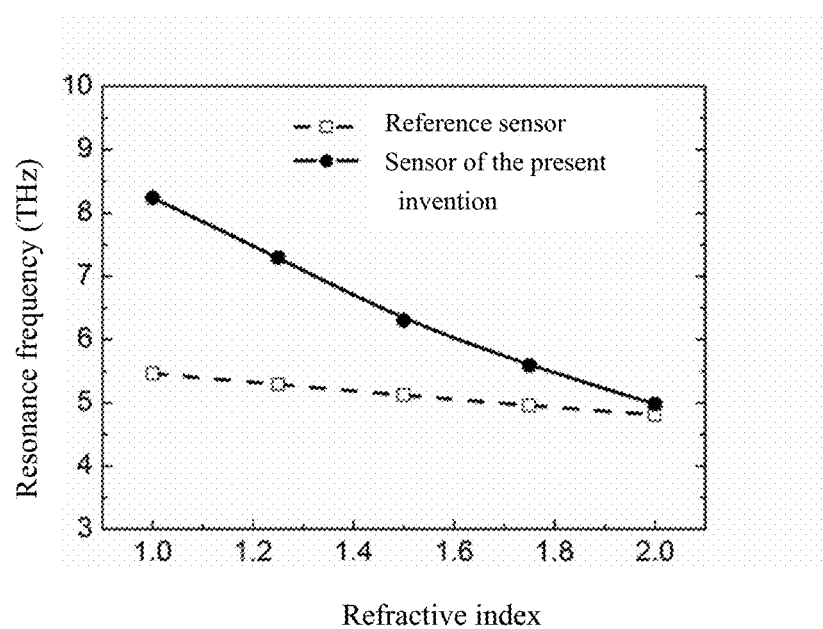
Figure 12A:
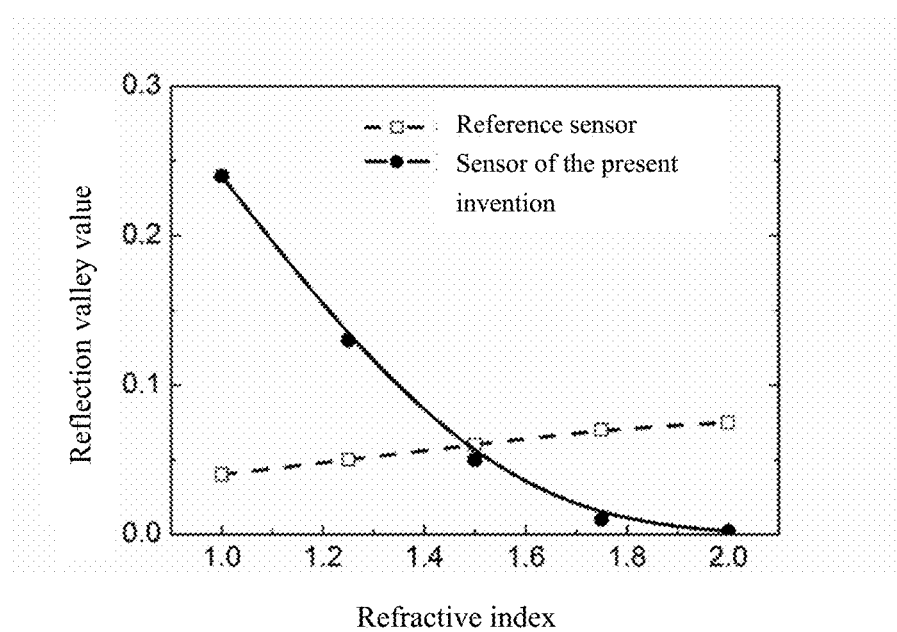
FIG. 12a to FIG. 12b are views showing the relation between the reflectivity of the terahertz sensor and the refractive index of liquid, in a case where the cover layer is a non-destructive medium (a) and a case where the cover layer is a destructive medium (b), according to an optional implementation.
Figure 12B:
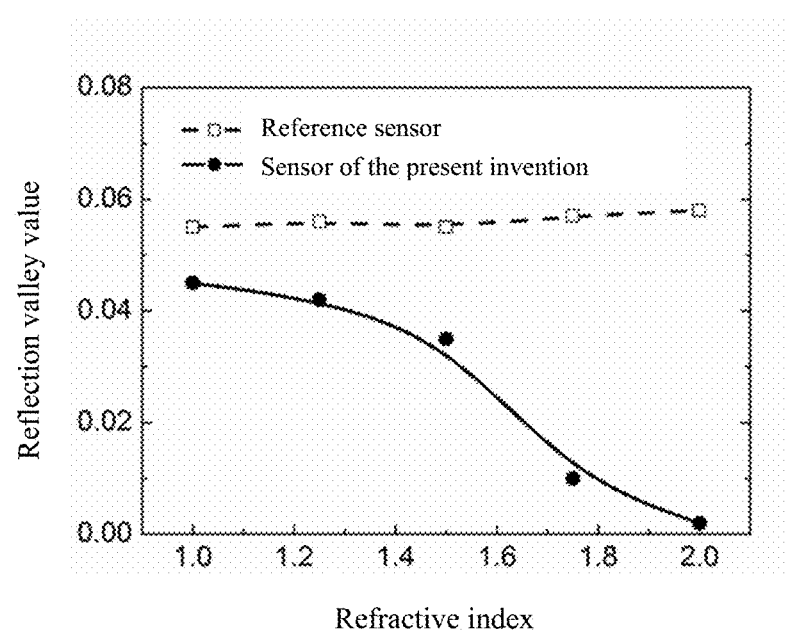
Figure 13:
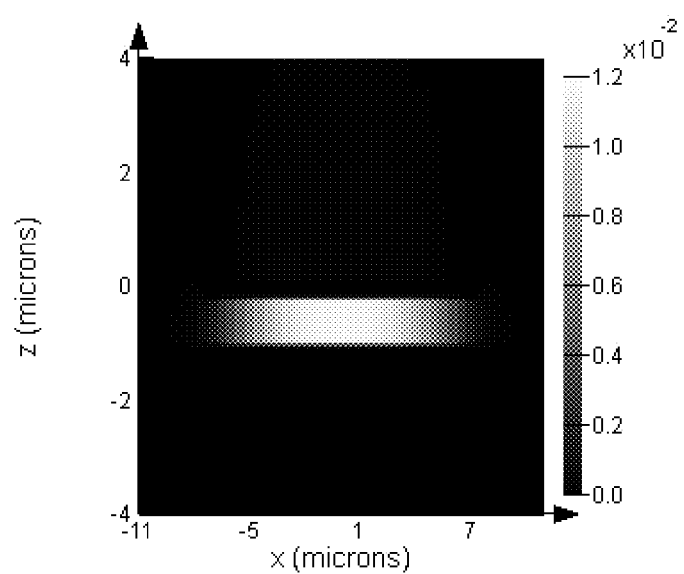
FIG. 13 shows an Hy field distribution corresponding to a formant of the terahertz sensor according to an optional implementation.

In this embodiment, the metal plane reflector 2, the liquid to be tested in the micro-fluidic channel 6 and the metal microstructure layer 4 form a composite structure having resonance absorption properties, and may form a perfect absorber 90. As shown in FIG. 10, the reflectivity at a resonance frequency is less than 1%, that is, the absorbency is approximately 100%. It can be known from the Hy distribution of the magnetic field in the y-direction that, the magnetic field is spatially localized in the micro-fluidic channel, and very sensitive to the refractive index of liquid to be tested in the micro-fluidic channel. Meanwhile, a sensor in which a micro-fluidic channel is integrated on the surface of a metal microstructure layer, as shown in FIG. 9, is selected for conference and comparison. Referring to FIG. 11a and FIG. 12a, those drawings are views showing change in the resonance frequency and the reflectivity of the terahertz micro-fluid channel sensor with the refractive index of liquid to be tested in the fluid channel 6. The sensitivity of the sensor in such a structure is 0.65 THz/RIU, while the sensitivity of the sensor of the present invention is 3.44 THz/RIU, which is 5.3 times of that of the reference structure, and the detection of the refractive index of liquid to be tested is limited to 0.0014 RIU (calculated assuming that the spectral resolution of a terahertz spectrometer is 5 GHz); and the reflectivity at the formant changes with the refractive index by 24%, and is 6 times of that of the reference structure (the reflectivity changes by 4%). And, when the PDMS is regarded as a destructive medium, change in the resonance frequency of the terahertz micro-fluidic sensor of the present invention is the same as that when the PDMS is regarded as a non-destructive medium (FIG. 11b), and the change in the reflectivity (4.2%) is 14 times of that of the reference structure (the reflectivity changes by 0.3%) (FIG. 12b).

Embodiment 2

Figure 14:
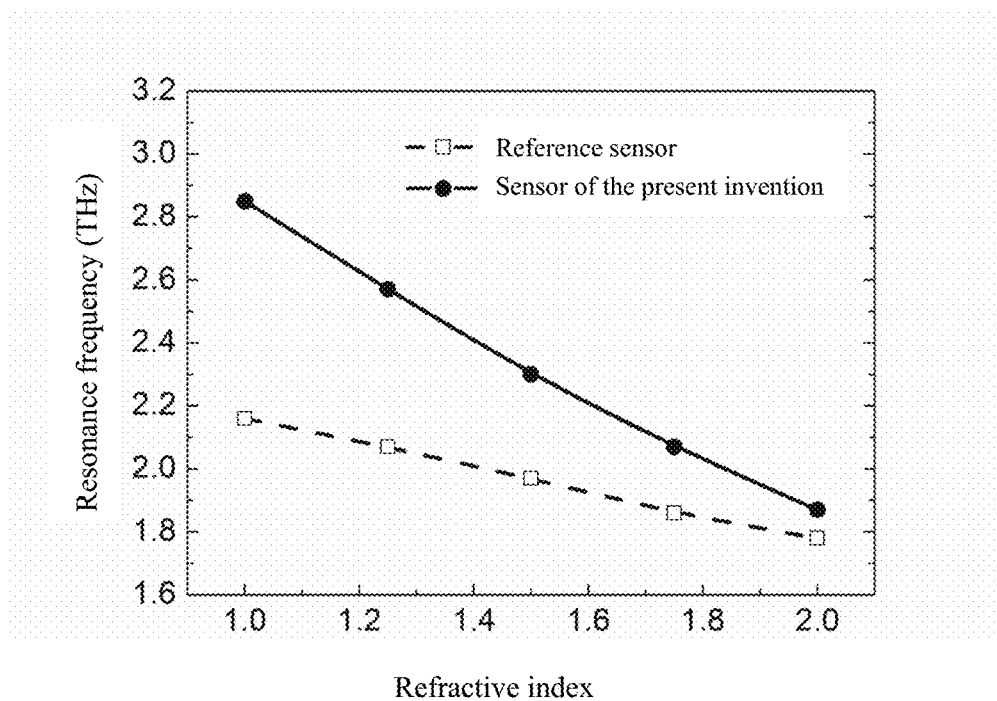
FIG. 14 is a view showing the relation between the resonance frequency of the terahertz sensor and the refractive index of liquid according to still another implementation.
Figure 15:
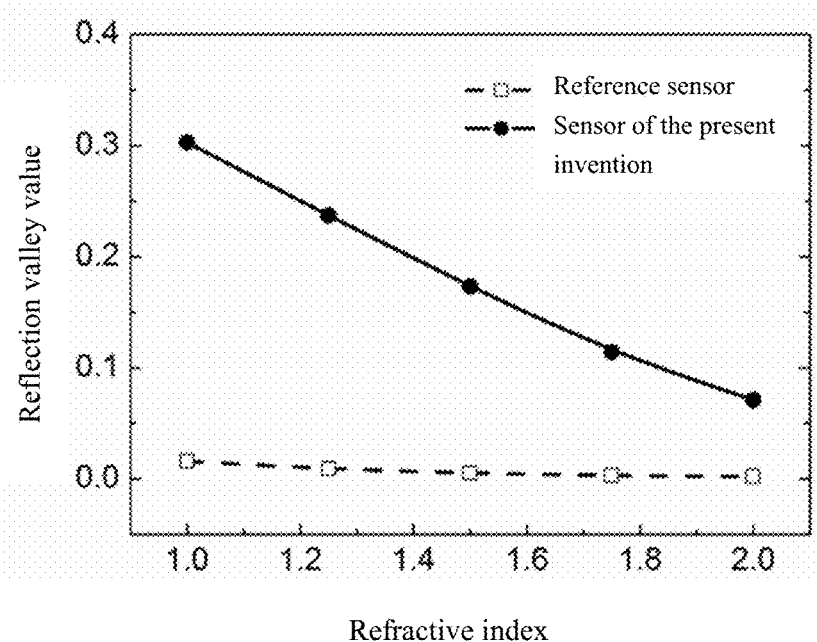
FIG. 15 is a view showing the relation between the reflectivity of the terahertz sensor and the refractive index of liquid according to still another implementation.

The structures and processes in this embodiment are the same as those in Embodiment 1. As another preferred structure parameter, the metal microstructure layer 4, which is of a crisscross structure, has a period of 56 µm, an arm length of 40 µm, and an arm width of 4 µm. The height of the fluid channel 6 is 4 µm. It may be known from the relation (FIG. 14 and FIG. 15) between the resonance frequency and reflectivity and the change in the refractive index of liquid in the fluid channel 6 that, the resonance results in strong absorption, and results in change in the resonance frequency and reflectivity when the refractive index of liquid in the fluid channel 6 changes. The terahertz micro-fluidic channel sensor of the present invention has a sensitivity of 0.98 THz/RIU, which is 2.5 times of that of the sensor with the micro-fluidic channel integrated on the surface of the metal microstructure layer (the sensitivity is 0.38 THz/RIU); and meanwhile, change in the reflectivity with the refractive index at the formant is relatively improved by 15 times.

Embodiment 3

Figure 6:
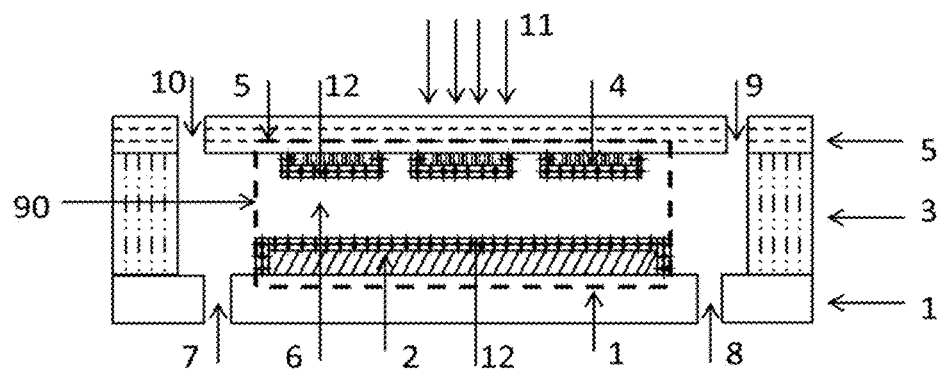
FIG. 6 is a schematic longitudinal cross-section view of the high-sensitivity terahertz micro-fluidic channel sensor according to another optional implementation of the present invention.

Referring to FIG. 6, a schematic longitudinal cross-section view of the high-sensitivity terahertz micro-fluidic channel sensor according to this embodiment is shown. The difference from Embodiment 1 is that a medium protection layer 12, for example, silicon dioxide, silicon nitride, aluminum oxide and SU-8 photoresist, is contained on surfaces of the metal plane reflector 2 and the metal microstructure layer 4, and the thickness of the medium protection layer 12 is 10 nm to 100 nm. The medium protection layer 12 introduced in the structure can better improve the stability of the terahertz micro-fluidic channel sensor.

Embodiment 4

Figure 7:
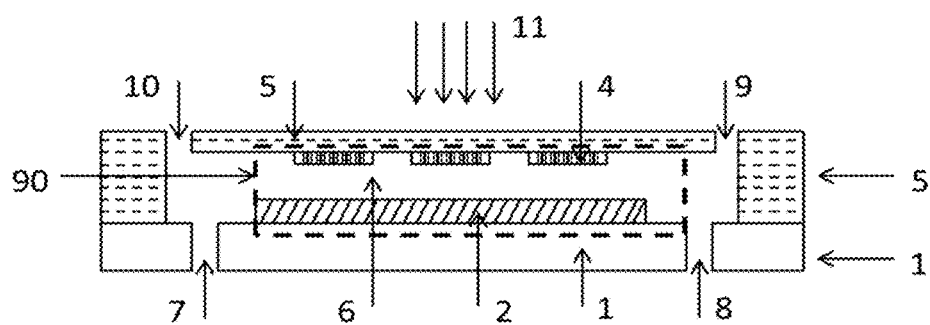
FIG. 7 is a schematic longitudinal cross-section view of the high-sensitivity terahertz micro-fluidic channel sensor according to still another optional implementation of the present invention.

In this embodiment, description will be given by taking the schematic longitudinal cross-section view of the high-sensitivity terahertz micro-fluidic channel sensor as shown in FIG. 7. The difference from the aforementioned embodiments is that the micro-fluidic channel 6 is prepared on the substrate 1 and/or the cover layer 5 by micro-nano machining process, the height of the micro-fluidic channel 6 is 1 µm to 10 µm, and the width thereof is 100 µm to 5000 µm; then, the metal reflector 2 is prepared on the substrate 1 and the metal microstructure layer 4 is prepared on the cover layer 5 by micro-nano machining process, so that the metal reflector 2 and/or the metal microstructure layer 4 are located in the micro-fluidic channel 6. In this structure, the substrate 1 is bonded to the cover layer 5 by directly bonding (without any bonding material layer 3); a hollow channel, which is closed all around, is formed between the substrate 1 and the cover layer 5; and finally, holes are dilled on the substrate 1 and the cover layer 5 and communicated to the channel, to form the liquid channel for inputting and outputting.

Embodiment 5

Figure 4:
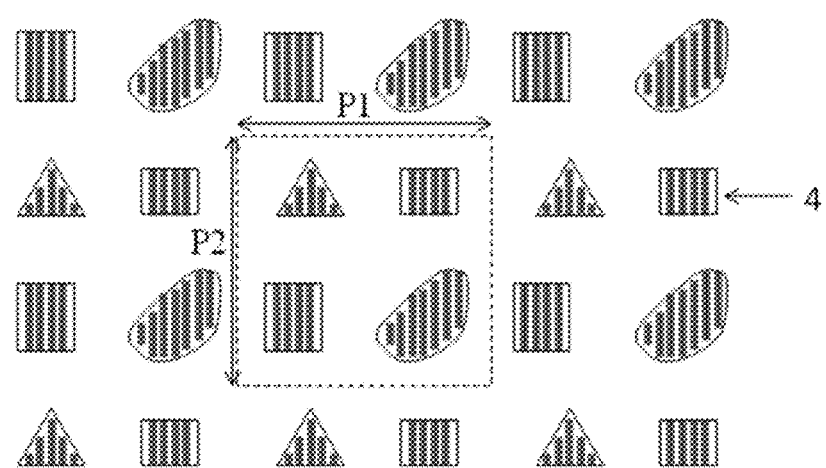
FIG. 4 is a schematic plan view of the two-dimensional periodic structure of the metal microstructure layer according to another optional implementation of the present invention.

This embodiment is similar to Embodiment 1, with the difference in that the metal microstructure layer 4 in this embodiment, similarly to that as shown in FIG. 4, uses a combination of two simple units which correspondingly generate two absorption peaks.

Figure 16:
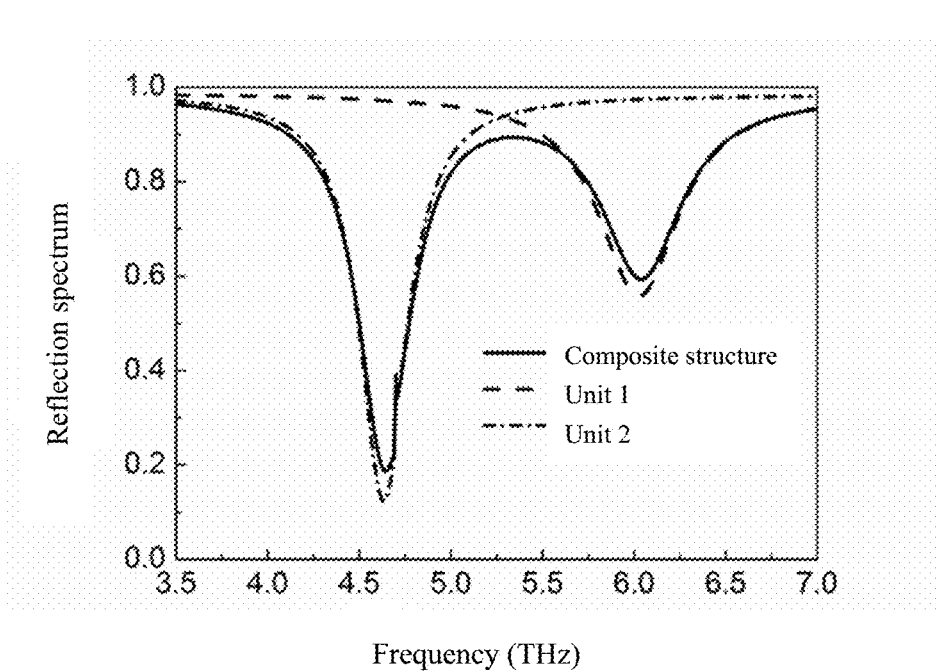
FIG. 16 is a reflection spectrum of the terahertz sensor, in a case where the metal microstructure layer is a single unit and a composite structure of units, according to an optional implementation.
Figure 17:
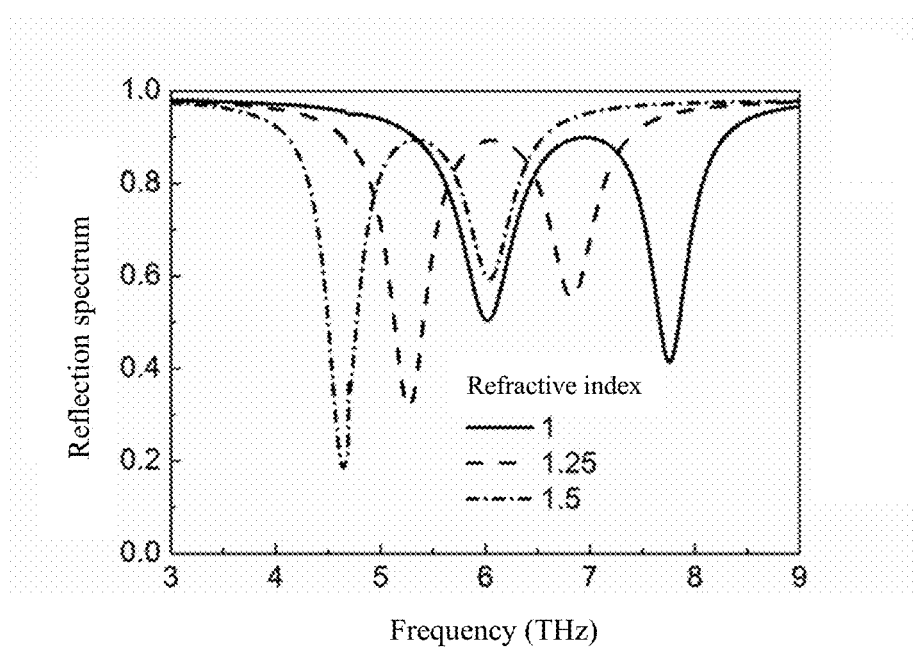
FIG. 17 is a reflection spectrum of terahertz sensors corresponding to different refractive indexes of liquid according to still another optional implementation.

As still another preferred structure parameter, the metal microstructure layer 4, which is of a crisscross structure, has an arm length of unit 1 of 15 µm, an arm length of unit 2 of 20 µm, and an arm width of both unit 1 and unit 2 of 4 µm. The period in the X-direction is 44 µm, the period in the Y-direction is 22 µm, and the height of the fluid channel 6 is 2 µm. The results of calculation are shown in FIG. 16. It can be seen that two resonance frequencies of the composite structure correspond to the resonance frequency of the signal unit. FIG. 17 shows change in reflection spectrum of the terahertz sensor of the composite structure with the refractive index. It can be seen that both the frequency and reflectivity of the two formants change when the refractive index of liquid in the flow channel changes. As a result, the accuracy of detection of sensors may be further improved.

Embodiment 6

Figure 8:
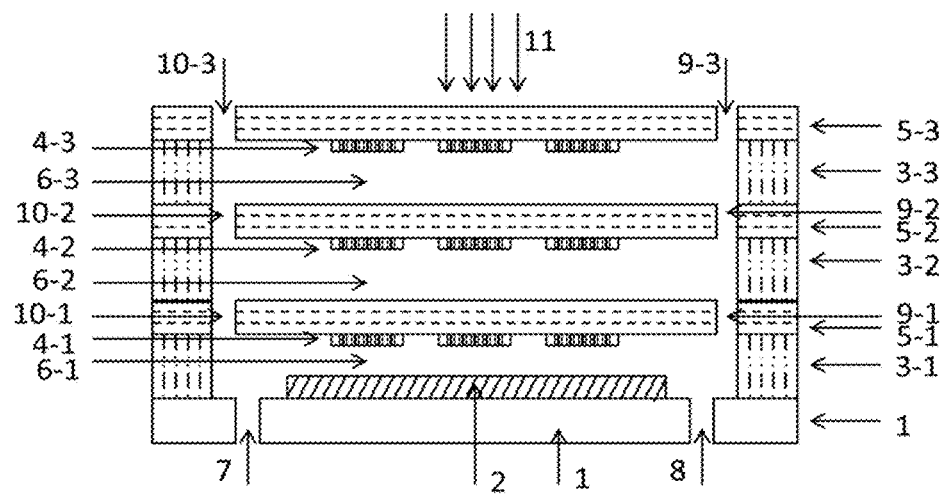
FIG. 8 is a schematic longitudinal cross-section view of the high-sensitivity terahertz micro-fluidic channel sensor according to yet another optional implementation of the present invention.
Figure 18:
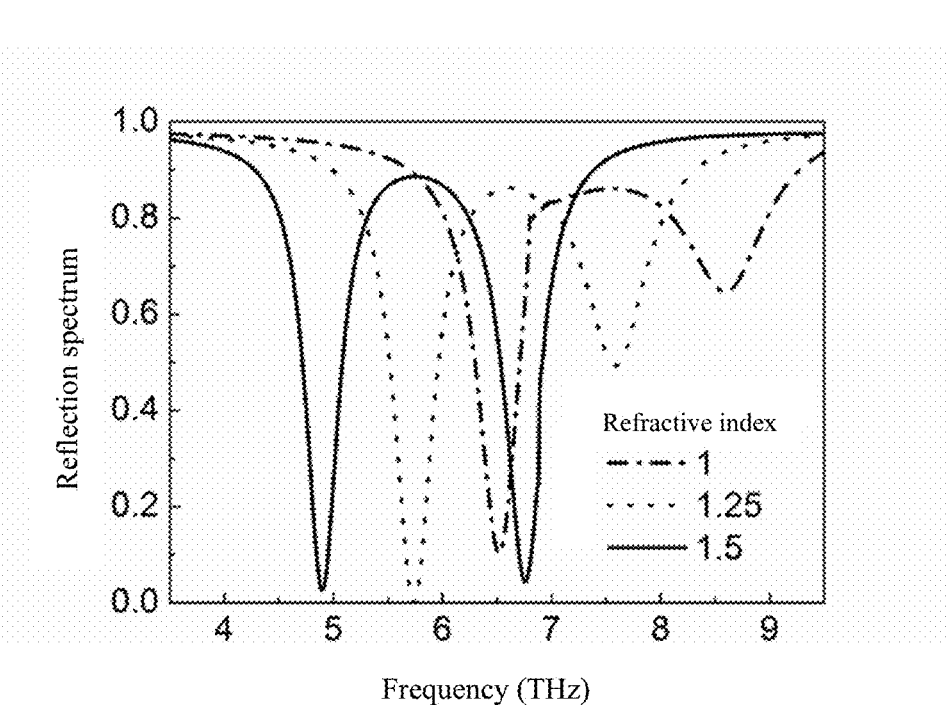
FIG. 18 is a reflection spectrum of terahertz sensors corresponding to different refractive indexes of liquid according to yet still another optional implementation.

As shown in FIG. 8, in the terahertz micro-fluidic channel sensor of the present invention, a plurality of different metal microstructure layers 4 and micro-fluidic channels 6 may be cascaded in a direction perpendicular to the plane direction of the micro-fluidic channel. In this embodiment, FIG. 8 shows a terahertz micro-fluidic channel sensor using two cascaded structures. As a preferred structure parameter, the metal microstructure layers 4-1 and 4-2, which are of crisscross structures, have an arm length of 20 µm and 14 µm, an arm width of 6 µm, and a period of 30 µm. The height of the micro-fluidic channels 6-1 and 6-2 is 1 µm. The micro-fluidic channels 6-1, 6-2, 6-3, are in communication with each other through vertical inlets/outlets 10-1, 10-2, 9-1, 9-2. FIG. 18 shows change in reflection spectrum of the terahertz sensor of the cascaded structure with the refractive index. It can be seen that two high resonance frequencies due to resonance shift with the change in the refractive index of liquid in the fluid channel 6. High-sensitivity detection may be realized.

Embodiment 7

Figure 19:
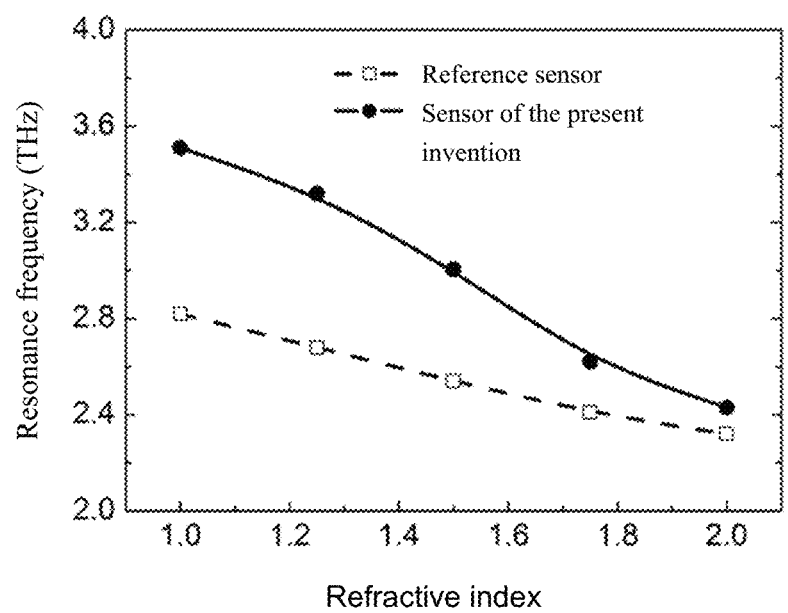
FIG. 19 is a view showing the relation between the resonance frequency of the terahertz sensor and the refractive index of liquid according to still another implementation.

This embodiment is similar to Embodiment 1, with the difference in that the cover layer 5 is formed of high-resistance silicon and PDMS. As still another preferred structure parameter, the metal microstructure layer 4, which is of a crisscross structure, has a period of 40 μm, an arm length of 30 μm and an arm width of 10 μm. The cover layer 5 is formed of high-resistance silicon with a thickness of 300 μm and a destructive medium PDMS with a thickness of 20 μm. The height of the fluid channel 6 is 3 μm. It can be seen from the relation (FIG. 19) between change in the resonance frequency with the refractive index of liquid in the fluid channel 6 that, the resonance frequency changes when the refractive index of liquid in the fluid channel 6 changes. The terahertz micro-fluidic channel sensor of the present invention has a sensitivity of 1.13 THz/RIU, which is 2.7 times of that (0.42 THz/RIU) of a sensor with the micro-fluidic channel integrated on the surface of the metal microstructure layer.

It should be understood that those disclosed in the present invention is one or more preferred embodiments, and any partial changes or modifications easily to be deduced by those skilled in the art, as they are derived from the technical concept of the present invention, shall be regard as not departing from the patent right scope of the present invention.

The invention claimed is:

1. A high-sensitivity terahertz micro-fluidic channel sensor, comprising: a substrate having a metal plane reflector; at least one cover layer having a metal microstructure layer attached thereon, the at least one cover layer being attached to the substrate and the metal microstructure layer facing the metal plan reflector and separate from the metal plan reflector; and at least one micro-fluidic channel, formed between the metal plane reflector on the substrate and the metal microstructure layer on the at least one cover layer, for a liquid to be tested to flow through, wherein the metal microstructure layer is disposed inside the at least one micro-fluidic channel.

2. The high-sensitivity terahertz micro-fluidic channel sensor according to claim 1, comprising:
   more than two cover layers successively distributed in a direction perpendicular to a plane direction of the at least one micro-fluidic channel; and
   a metal microstructure layer is provided on a surface of each cover layer, facing the metal plane reflector;
   wherein there are at least two micro-fluidic channels formed between the metal plane reflector and an adjacent metal microstructure layer and between adjacent cover layers, and the at least two micro-fluidic channels are in communication with each other.

3. The high-sensitivity terahertz micro-fluidic channel sensor according to claim 2, characterized in the at least two micro-fluidic channels communicate with each other through vertical inlets/outlets.

4. The high-sensitivity terahertz micro-fluidic channel sensor according to claim 1, characterized in that the metal microstructure layer comprises more than one periodic structure units adhered on the cover layer; and the periodic structure units are separated from each other between 10 μm to 500 μm, and a thickness thereof is 0.01 μm to 0.5 μm.

5. The high-sensitivity terahertz micro-fluidic channel sensor according to claim 4, characterized in that metal used for forming the metal microstructure layer is selected from gold, silver, copper, aluminum, titanium, nickel and chromium or a combination of more than two thereof.

6. The high-sensitivity terahertz micro-fluidic channel sensor according to claim 1, characterized in that a thickness of the metal plane reflector is greater than 50 nm.

7. The high-sensitivity terahertz micro-fluidic channel sensor according to claim 6, characterized in that metal used for forming the metal plane reflector is selected from gold, silver, copper, aluminum, titanium, nickel and chromium or a combination of more than two thereof.

8. The high-sensitivity terahertz micro-fluidic channel sensor according to claim 1, characterized in that a height of the micro-fluidic channel is between 1 μm to 10 μm, and a width thereof is between 100 μm to 5000 μm; and two ends of the micro-fluidic channel are in communication with a liquid inlet and a liquid outlet of the sensor.

9. The high-sensitivity terahertz micro-fluidic channel sensor according to claim 1, characterized in that material for the substrate is selected from silicon, gallium arsenide, glass, polydimethylsiloxane, polypropylene, polyethylene, polytetrafluoroethylene, polymethylpentene and polyimide.

10. The high-sensitivity terahertz micro-fluidic channel sensor according to claim 1, characterized in that material for the cover layer is selected from silicon, gallium arsenide, glass, polydimethylsiloxane, polypropylene, polyethylene, polytetrafluoroethylene, polymethylpentene and polyimide.

11. The high-sensitivity terahertz micro-fluidic channel sensor according to claim 1, characterized in that the substrate is connected to an adjacent cover layer by bonding, adjacent cover layers are connected to each other by bonding, and a micro-fluidic channel is formed between the substrate and an adjacent cover layer and between adjacent cover layers.

12. The high-sensitivity terahertz micro-fluidic channel sensor according to claim 1, further comprising a medium protection layer formed on the metal plane reflector and/or the metal microstructure layer; and the medium protection layer having a thickness between 0 nm to 100 nm.

13. The high-sensitivity terahertz micro-fluidic channel sensor according to claim 12, characterized in that material used for forming the medium protection layer is selected from silicon dioxide, silicon nitride, aluminum oxide and SU-8 photoresist.

14. A method for preparing the high-sensitivity terahertz micro-fluidic channel sensor according to claim 1, comprising:
   forming a metal plane reflector on a substrate;
   forming a metal microstructure layer on at least one cover layer, the metal microstructure layer facing the metal plan reflector;
   connecting the substrate to the at least one cover layer to form at least one closed micro-fluidic channel between the substrate and the at least one cover layer, the metal microstructure layer and the metal plan reflector being exposed in the at least one closed micro-fluidic channel; and
   forming a through via, communicated to the micro-fluidic channel, on the substrate and/or the cover layer, to form a flow channel for inputting or outputting liquid to be tested to or from the sensor.

15. The method for preparing the high-sensitivity terahertz micro-fluidic channel sensor according to claim 14, comprising the following steps of:

forming the metal plane reflector on the substrate by a metal film deposition process;

forming the metal microstructure layer, or the metal microstructure layer and a side wall of the micro-fluidic channel, on the at least one cover layer by a micro-nano machining process;

connecting the substrate to the at least one cover layer by bonding to form at least one closed micro-fluidic channel between the substrate and the at least one cover layer; and forming a through via, communicated to the micro-fluidic channel, on the substrate and/or cover layer, physically or chemically.

* * * * *